(12) United States Patent
Han

(10) Patent No.: US 10,597,426 B2
(45) Date of Patent: Mar. 24, 2020

(54) POLYPEPTIDE COMPOUND AND PREPARATION METHOD AND USE THEREOF

(71) Applicants: BEIJING COISLITONG INDUSTRIAL CO., LTD., Beijing (CN); Su Han, Beijing (CN)

(72) Inventor: Su Han, Beijing (CN)

(73) Assignees: BEIJING COISLITONG INDUSTRIAL CO., LTD. (CN); Su Han (CN)

( * ) Notice: Subject to any disclaimer, the term of this patent is extended or adjusted under 35 U.S.C. 154(b) by 0 days.

(21) Appl. No.: 15/852,288

(22) Filed: Dec. 22, 2017

(65) Prior Publication Data

US 2018/0201653 A1    Jul. 19, 2018

Related U.S. Application Data

(63) Continuation of application No. PCT/CN2016/086856, filed on Jun. 23, 2016.

(30) Foreign Application Priority Data

Jun. 26, 2015  (CN) .......................... 2015 1 0364764

(51) Int. Cl.
| | | |
|---|---|---|
| C07K 14/00 | (2006.01) | |
| A61P 37/04 | (2006.01) | |
| A61K 38/10 | (2006.01) | |
| A61K 38/16 | (2006.01) | |
| C07K 1/04 | (2006.01) | |
| C07K 1/06 | (2006.01) | |
| C07K 7/08 | (2006.01) | |
| C07K 1/16 | (2006.01) | |
| A61K 38/00 | (2006.01) | |

(52) U.S. Cl.
CPC ............ *C07K 14/001* (2013.01); *A61K 38/10* (2013.01); *A61K 38/16* (2013.01); *A61P 37/04* (2018.01); *C07K 1/04* (2013.01); *C07K 1/042* (2013.01); *C07K 1/06* (2013.01); *C07K 1/061* (2013.01); *A61K 38/00* (2013.01); *C07K 1/16* (2013.01); *C07K 7/08* (2013.01)

(58) Field of Classification Search
CPC ........ C07K 14/005; A61P 31/18; A61P 35/00; A61P 37/04
See application file for complete search history.

(56) References Cited

U.S. PATENT DOCUMENTS 9,040,051 B2 * 5/2015 Schultze ................ A61K 35/17
424/141.1

FOREIGN PATENT DOCUMENTS

| CN | 101838305 A | 9/2010 |
|---|---|---|
| CN | 101899093 A | 12/2010 |
| CN | 102190713 A | 9/2011 |
| CN | 102666569 A | 9/2012 |
| CN | 102675410 A | 9/2012 |
| CN | 103159858 A | 6/2013 |
| WO | 2010080819 A1 | 7/2010 |

OTHER PUBLICATIONS

Bauer et al., Biochimica et Biophysica Acta, 1354, 1997, 183-188. (Year: 1997).*
PCT International Search Report and Written Opinion dated Sep. 19, 2016 from corresponding Application No. PCT/CN2016/086856, 10 pages.
Chang Rao et al., "Synthesis of Peptide Dendrimer", Journal of the American Chemical Society, vol. 116, No. 15, Jul. 1, 1994, pp. 6975-6976.
Supplementary Partial European Search Report; Application No. EP 16 81 3713; dated Jul. 25, 2019; 9 pages.

* cited by examiner

*Primary Examiner* — James H Alstrum-Acevedo
*Assistant Examiner* — Kaipeen E Yang
(74) *Attorney, Agent, or Firm* — Dilworth IP, LLC

(57) ABSTRACT

The invention discloses a polypeptide compound and a preparation method and application thereof. The polypeptide compound has a structural formula as follows: $(X_A X_B X_C X_D X_E\text{-}X)_2 KY$, or $\{(X_A X_B X_C X_D X_E\text{-}X)_2 K\}_2 KY$, or $\{(\{X_A X_B X_C X_D X_E\text{-}X\}_2 K)_2 K\}_2 KY$, where, $X_A$ is a polar amino acid molecule, $X_B$ and $X_E$ are alkaline amino acid molecules (the same or different), $X_C$ and $X_D$ are non-polar amino acid molecules (the same or different), K is lysine (Lys, K), and X and Y are null, or any one or more amino acid or chemical groups. The polypeptide compound provided in the invention has an effect of enhancing the immune function of a body and has an application potential of being developed into a clinical medicine capable of enhancing the immune function of a body.

25 Claims, 1 Drawing Sheet

POLYPEPTIDE COMPOUND AND PREPARATION METHOD AND USE THEREOF

FIELD OF THE INVENTION

The present invention relates to the bio-pharmaceutical field, in particular to a polypeptide compound molecule, a preparation method of the polypeptide compound, and an application of the polypeptide compound in preparation of medicines for enhancing immunity ability and the vaccine immune response ability of an animal body.

BACKGROUND OF THE INVENTION

The genetic genes of organisms are stored in poly deoxynucleotide chains, and proteins that execute biological functions are coded in the genetic genes. Various proteins exist in organisms and they execute different biological functions to maintain vital activities. Though there are numerous kinds of proteins, they are essentially composed of 20 kinds of naturally-occurring amino acids that exist in the natural world. Proteins differ significantly owing to the composition and sequence of these amino acids. Generally speaking, molecules that contain 50 or more amino acids are referred to as proteins, peptide chains that contain 10 or more amino acids are referred to as polypeptides, and peptide chains that contain less than 10 amino acids are referred to as oligopeptides. The smallest functional small-peptide discovered up to now only contains 2 amino acids. Usually, functional peptide fragments that are composed of 4 or more amino acids are commonly seen.

As the Human Genome Project has been completed and the Human Proteome Project has been developed, more and more functional protein segments will be discovered and applied as medicines in the bio-pharmaceutical field. A functional protein segment usually refers to a natural polypeptide segment that is found as having a specific biological function. Such a functional protein segment usually is a peptide segment composed of two to ten amino acids. The identified and discovered functional protein segments can be prepared via an artificial synthesis approach. Polypeptide medicines that have been developed and applied clinically include "oxytocin", "thymosin a1", and "thymopentin", etc. Polypeptide medicines available presently include "octreotide", which is prepared through artificial modification of natural peptide chains and used to treat hemorrhage of the digestive tract and acromegaly, and "hirudin peptide", which has an anti-coagulation effect. The functional segments in proteins often can be screened for polypeptide segments that contain tens of amino acids or even as few as two amino acids. These functional segments set a basis for artificial synthesis and application of functional polypeptide segments.

In proteins, polypeptides or oligopeptides, the deletion, addition or substitution of a single amino acid, the blocking of an amino terminal (N terminal) or carboxyl terminal (C terminal) amino acid, or the addition of any chemical group into the sequence or at the free end, etc., might result in changes of the original biological activity of the proteins, polypeptides, or oligopeptides. Designing, screening, and discovering new functional peptide fragments or seeking for efficient peptide fragments is an important link in the development of medicines.

BRIEF DESCRIPTION OF THE DRAWINGS

FIG. 1 shows the purification process.

CONTENTS OF THE INVENTION

To overcome the technical defects in the prior art, in a first aspect, the present invention provides a branched polypeptide compound, which has a structural formula expressed as $(X_AX_BX_CX_DX_E\text{-}X)_2KY$, or $\{(X_AX_BX_CX_DX_E\text{-}X)_2K\}_2KY$, or $\{(\{X_AX_BX_CX_DX_E\text{-}X\}_2K)_2K\}_2KY$; where, $X_A$ is a polar amino acid molecule, $X_B$ and $X_E$ are alkaline amino acid molecules (the same or different), $X_C$ and $X_D$ are non-polar amino acid molecules (the same or different), K is lysine (Lys, K), and X and Y are null, or one or more amino acid molecules or chemical groups.

The $(X_AX_BX_CX_DX_E\text{-}X)_2KY$ structure is shown in formula 4:

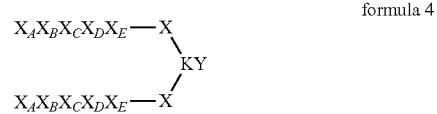

formula 4

The $\{(X_AX_BX_CX_DX_E\text{-}X)_2K\}_2KY$ structure is shown in formula 5:

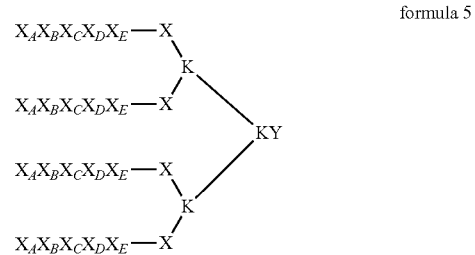

formula 5

The $\{(\{X_AX_BX_CX_DX_E\text{-}X\}_2K)_2K\}_2KY$ structure is shown in formula 6:

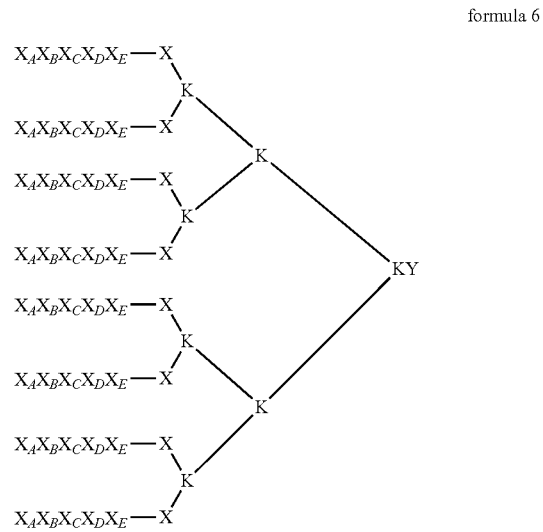

formula 6

Where, X and Y are null, or any amino acid, or peptide fragments composed of any number of amino acids, or chemical groups that can connect amino acids or peptide fragments, and X and Y may be the same or different from each other; for example, X may be null, and Y may be glycine (Gly, G).

$X_A$ is selected from polar amino acids, and may be cysteine (Cys, C), glycine (Gly, G), serine (Ser, S), threonine (Thr, T), tyrosine (Tyr, Y), asparagine (Asn, N), or glutamine (Gln, Q); preferably is cysteine (Cys, C), serine (Ser, S), threonine (Thr, T), tyrosine (Tyr, Y), asparagine (Asn, N), or glutamine (Gln, Q); $X_A$ more preferably is cysteine (Cys, C), serine (Ser, S), threonine (Thr, T), or glutamine (Gln, Q).

$X_B$ and $X_E$ are selected from alkaline amino acids, and may be arginine (Arg, R), lysine (Lys, K), or histidine (His, H) respectively, and may be the same or different from each other; $X_B$ preferably is arginine (Arg, R) or lysine (Lys, K).

$X_C$ and $X_D$ are selected from non-polar amino acids, and may be alanine (Ala, A), valine (Val, V), leucine (Leu, L), isoleucine (Ile, I), proline (Pro, P), phenylalanine (Phe, F), tryptophan (Trp, W), or methionine (Met, M) respectively, and may be the same or different from each other; $X_C$ preferably is alanine (Ala, A), valine (Val, V), leucine (Leu, L), isoleucine (Ile, I), proline (Pro, P), phenylalanine (Phe, F), or tryptophan (Trp, W), $X_C$ more preferably is alanine (Ala, A), leucine (Leu, L), isoleucine (Ile, I) or proline (Pro, P); and $X_D$ preferably is leucine (Leu, L), isoleucine (Ile, I) or proline (Pro, P).

The present invention further includes a derivative produced through chemical modification and restructuring of the polypeptide compound, for example:

A salt compound formed by the polypeptide compound with an organic acid or inorganic acid;

An ether, ester, glucoside, or glycoside compound, etc., which may be formed by the hydroxyl included in the polypeptide compound, but is not limited to compounds formed in such a way;

A thioether or thioglycoside compound, which may be formed by the sulfhydryl included in the polypeptide compound, or a compound containing disulfide bonds, which may be formed by the sulfhydryl included in the polypeptide compound with cysteine or peptide containing cysteine, but is not limited to compounds formed in such a way;

An acylate or alkylate compound, which may be formed by the amido group included in the polypeptide compound, or a glucoside compound, etc., which may be formed by the amino group included in the polypeptide compound with saccharides, but is not limited to compounds formed in such a way;

An ester or amide compound, etc., which may be formed by the carboxyl group included in the polypeptide compound, but is not limited to compounds formed in such a way;

A glucoside, acylate, or alkylate compound, etc., which may be formed by the imino group included in the polypeptide compound, but is not limited to compounds formed in such a way;

An ester, ether, glucoside, or glycoside compound, which may be formed by the phenolic hydroxyl group included in the polypeptide compound, or a salt compound, which may be formed by the phenolic hydroxyl group included in the polypeptide compound with organic alkali or inorganic alkali compounds, but is not limited to compounds formed in such a way;

A coordinate, clathrate, or chelate compound formed by the polypeptide compound with metal ions;

A hydrate or solvent formed by the polypeptide compound.

In a second aspect, the present invention provides a pharmaceutical composition that contains the above-mentioned polypeptide compound, a geometrical isomer of the pharmaceutical composition, a pharmaceutically acceptable salt or solvated compound of the pharmaceutical composition, and the pharmaceutical composition in a form of pharmaceutical carrier or excipient.

In a third aspect, the present invention provides a method for preparing the above-mentioned polypeptide compound, in which a synthesis route of $(X_A X_B X_C X_D X_E-X)_2 KY$ is expressed by formula 1:

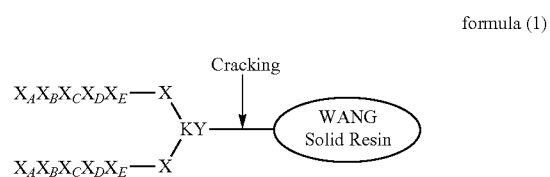

formula (1)

Y is covalently attached to a WANG solid resin first, and then is connected with lysine (Lys, K) by condensation;

Next, the two terminal amino groups of K in KY are bonded with two $X_A X_B X_C X_D X_E$-X segments to form a two-branch peptide $(X_A X_B X_C X_D X_E-X)_2$KY-WANG solid resin complex, wherein, the $X_A X_B X_C X_D X_E$-X segments may be synthesized first and then condensed with the WANG solid resin-YK, or X, $X_E$, $X_D$, $X_C$, $X_B$ and $X_A$ may be bonded in sequence on the basis of the WANG solid resin-YK;

Finally, the two-branch peptide is cleaved from the WANG solid resin, to obtain a polypeptide compound $(X_A X_B X_C X_D X_E-X)_2$KY with two copies of the polypeptide $X_A X_B X_C X_D X_E$-X.

The synthesis route of $\{(X_A X_B X_C X_D X_E-X)_2 K\}_2 KY$ structure is expressed by formula 2:

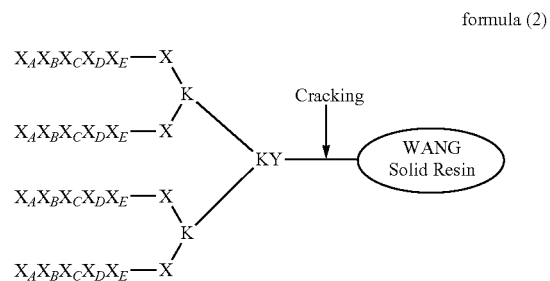

formula (2)

Y is covalently attached to the WANG solid phase first, and then is connected with lysine (Lys, K) by condensation, to form a KY-WANG solid resin complex;

Then, the two amino terminals of K in KY are connected with the terminal carboxyl groups of another two lysines K by condensation, to form a two-branch skeleton $K_2$KY-WANG solid resin;

Next, the two amino terminals of each lysine K in "$K_2$" are connected with an $X_A X_B X_C X_D X_E$-X segment respectively by condensation, to form a four-branch peptide $\{(X_A X_B X_C X_D X_E-X)_2 K\}_2$KY-WANG solid resin complex;

Finally, the four-branch peptide is cleaved from the WANG solid resin, to obtain a polypeptide compound $\{(X_A X_B X_C X_D X_E-X)_2 K\}_2$KY with four copies of the polypeptide $X_A X_B X_C X_D X_E$-X.

The synthesis route of the $\{(\{X_AX_BX_CX_DX_E\text{-}X\}_2K)_2K\}_2KY$ structure is expressed by formula 3:

formula (3)

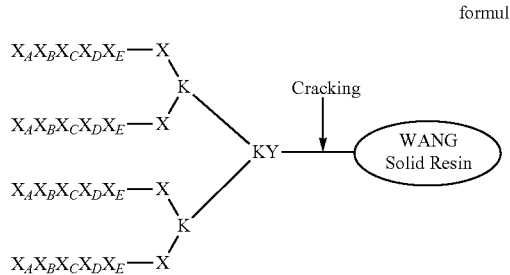

Y is covalently attached to the WANG solid phase first, and then is connected with lysine (Lys, K) by condensation, to form KY-WANG solid resin;

Then, the two terminal amino groups of K in KY are bonded with the carboxyl terminals of another two lysines K by condensation, to form a two-branch skeleton $K_2KY$-WANG solid resin complex;

Then, the two terminal amino groups of each K in "$K_2$" in the $K_2KY$-WANG solid resin complex are bonded with the terminal carboxyl groups of the other two lysines K by condensation, to form a four-branch skeleton $K_4K_2KY$-WANG solid resin complex;

Next, the two terminal amino groups of each lysine K in "$K_4$" are bonded with an $X_AX_BX_CX_DX_E\text{-}X$ segment respectively by condensation, to form an eight-branch peptide $\{(\{X_AX_BX_CX_DX_E\text{-}X\}_2K)_2K\}_2KY$-WANG solid resin complex;

Finally, the eight-branch peptide is cleaved from the WANG solid resin, to obtain a polypeptide compound $\{(\{X_AX_BX_CX_DX_E\text{-}X\}_2K)_2K\}_2KY$ with eight copies of the polypeptide $X_AX_BX_CX_DX_E\text{-}X$.

Before the terminal carboxyl group of K is condensed with the Y-WANG solid resin, the two amido groups of K must be protected, preferably with at-butyloxycarbonyl (Boc) protection method/group or a fluorenylmethoxycarbonyl (Fmoc) protection method/group.

Before the carboxyl terminals of the other two lysines are condensed with the two amido terminals of K in KY, the two amino groups of each lysine must be protected; before the carboxyl terminal of the $X_AX_BX_CX_DX_E\text{-}X$ is condensed with the amido terminal of each lysine, the amino group of the $X_AX_BX_CX_DX_E\text{-}X$ must be protected, preferably with a t-butyloxycarbonyl (Boc) protection method/group or a fluorenylmethoxycarbonyl (Fmoc) protection method/group.

Specifically, the steps are as follows:

Step 1: protecting the two amino groups of the lysine K with an Fmoc protection method/group;

Step 2: fixing KY to the WANG solid resin with an automatic polypeptide synthesizer, in the following bonding sequence: WANG solid resin-YK;

When the two-copy polypeptide compound is prepared, the two activated terminal amino groups of lysine in KY are further condensed with another two $X_AX_BX_CX_DX_E\text{-}X$ fragments, to obtain the polypeptide compound $(X_AX_BX_CX_DX_E\text{-}X)_2KY$ with two copies of $X_AX_BX_CX_DX_E\text{-}X$, which are connected to the WANG solid resin; or the two activated terminal amino groups of the lysine K are further condensed with another two lysines K, in each of which the two amido groups have been protected with an Fmoc protection method, to obtain a two-branch skeleton $(X_AX_BX_CX_DX_E\text{-}X)_2KY$-WANG solid resin complex;

When the four-copy polypeptide compound is prepared, the two activated amino terminals of lysine in the two-branch skeleton "KY-WANG solid resin" are further condensed with two lysine molecules and then $X_AX_BX_CX_DX_E\text{-}X$ fragments, to obtain the polypeptide compound $\{(X_AX_BX_CX_DX_E\text{-}X)_2K\}_2KY$ with four copies of $X_AX_BX_CX_DX_E\text{-}X$, which is connected to the WANG solid resin; or the two activated terminal amino groups of each lysine in the two-branch skeleton The "KY-WANG solid resin" complex is further condensed with another two lysines K, in each of which the two amido groups have been protected with an Fmoc protection method/group, and one by one the amino acids condensed to make the $X_AX_BX_CX_DX_E\text{-}X$ fragment obtain a four-branch skeleton $(X_AX_BX_CX_DX_E\text{-}X)_4 K_2KY$-WANG solid resin complex;

When the eight-copy polypeptide compound is prepared, the two activated terminal amino groups of each lysine in the four-branch skeleton "$K_2KY$-WANG solid resin" complex are further condensed with Lysine and $X_AX_BX_CX_DX_E\text{-}X$ fragments, to obtain the polypeptide compound $\{(\{X_AX_BX_CX_DX_E\text{-}X\}_2K)_2K\}_2KY$ with eight copies of $X_AX_BX_CX_DX_E\text{-}X$, which is connected to the WANG solid resin;

Finally, the target polypeptide compound is cleaved from the WANG solid resin with a TFA method, to obtain a crude polypeptide compound product;

Step 3: the crude polypeptide compound product is purified with a chromatographic column (model: Daiso C18, 10 μm, 100 Å, 50×250 mm), wherein the mobile phase A is an aqueous solution that contains 0.05% trifluoroacetic acid and 2% acetonitrile, the mobile phase B is 90% acetonitrile/water, the flow rate is 25 mL/min., and the ultraviolet detection wavelength is 220 nm; the eluting peak solution is collected and then rough freeze-dried, to obtain a white flocculent polypeptide compound.

In a fourth aspect, the present invention provides an application of the above-mentioned polypeptide compound in preparation of immunization medicines for humans or animals or medicines for enhancing the immune function of humans or animals.

In a fifth aspect, the present invention provides an application of a polypeptide compound prepared with the above-mentioned method in preparation of immunization medicines for humans or animals or medicines for enhancing the immune function of humans or animals.

In a sixth aspect, the present invention provides an application of the above-mentioned polypeptide compound or a polypeptide compound prepared with the above-mentioned method in preparation of medicines for inhibiting tumor growth in human or animal bodies.

The tumor is a solid tumor (or residual tumor after medical operation) or a hematological tumor (including leukemia and lymphoma) in a human body.

The tumor includes but is not limited to sarcoma, liver cancer, colon cancer, lung cancer, stomach cancer, mammary cancer, and cervical cancer.

In a seventh aspect, the present invention provides an application of the above-mentioned polypeptide compound or a polypeptide compound prepared with the above-mentioned method in preparation of anti-infection or anti-virus medicines for humans or animals.

In an eighth aspect, the present invention provides an application of the above-mentioned polypeptide compound or a polypeptide compound prepared with the above-mentioned method in molecular tracers.

In a ninth aspect, the present invention provides an application of the above-mentioned polypeptide compound or a polypeptide compound prepared with the above-mentioned method in preparation of medicines for treating diseases of humans incurred by vascular proliferation (including, but not limited to application of medicines for treating maculopathy in fundus).

In the polypeptide compounds provided in the present invention, five multi-copy amino acid molecules in three kinds (polar amino acid molecules, alkaline amino acid molecules and non-polar amino acid molecules) are bonded via covalent bonds to form a branched polypeptide compound. The polypeptide compound is hopeful to be an effective ingredient in a variety of medicines, and is applicable to preparation of medicines for preventing and treating many diseases. Especially, the polypeptide compound will be widely applied in preparation of medicines for enhancing immunity ability, and can also be used as a molecular tracer in inhibition of vascularization.

The polypeptide compound described in the present invention is insensitive to catabolic enzymes in a physiological environment, since it has a non-natural molecular structure. Therefore, the effective half-life of the polypeptide compound in organisms can be prolonged effectively, and thereby the biological effect of the polypeptide compound can last for longer time in the body.

DETAILED DESCRIPTION OF THE EMBODIMENTS

In the present invention, a branched polypeptide molecule $(X_A X_B X_C X_D X_E\text{-}X)_2 KY$, $\{(X_A X_B X_C X_D X_E\text{-}X)_2 K\}_2 KY$ or $\{(\{X_A X_B X_C X_D X_E\text{-}X\}_2 K)_2 K\}_2 KY$, which contains multiples copies of $X_A X_B X_C X_D X_E\text{-}X$, is designed and prepared, wherein, $X_A$ is a polar amino acid molecule, and may be cysteine (Cys, C), glycine (Gly, G), serine (Ser, S), threonine (Thr, T), tyrosine (Tyr, Y), asparagine (Asn, N), or glutamine (Gln, Q); $X_B$ and $X_E$ are alkaline amino acid molecules (the same or different), may be one or two of arginine (Arg, R), lysine (Lys, K), or histidine (His, H), and may be the same or different from each other; $X_C$ and $X_D$ are non-polar amino acid molecules (the same or different), may be one or two of alanine (Ala, A), valine (Val, V), leucine (Leu, L), isoleucine (Ile, I), proline (Pro, P), phenylalanine (Phe, F), tryptophan (Trp, W), and methionine (Met, M), and may be the same or different from each other; K is lysine Fmoc-Lys(Fmoc)-OH that contain two active amino groups, X and Y are null, or any amino acid, or peptide fragments composed by any number of amino acids, or chemical groups that can bond up amino acids and peptide fragments. By changing the kinds of $X_A$, $X_B$, $X_C$, $X_D$ and $X_E$, the polypeptide compound provided in the present invention can be adapted to treat a variety of diseases. Especially, the polypeptide compound provided in the present invention can enhance humoral immunity and cellular immunity ability of human or animal bodies. Thus, a medicine for enhancing immune function in clinical application (for humans or animals) can be developed from the polypeptide compound provided in the present invention.

In 1963, an American scientist R. B. Merrifield invented a solid-phase synthesis method for extending a peptide chain by fixing the carboxyl terminal (C terminal) of amino acids in a target peptide to insoluble resin and controlling the amino terminal (N terminals) of amino acids bonded to the resin to have a condensation reaction with the carboxyl terminal of amino acids to be bonded; that is to say, the amino acids are condensed one by one starting from the carboxyl terminal (C terminal) of the polypeptide and extend continuously towards the amino terminal (N terminal) of the polypeptide fragment. Therefore, when the condensation reaction of the amino acids is executed, the amido and side chain groups of the amino acids to be bonded must be protected to avoid reaction of them. At present, commonly used protection methods include t-butyloxycarbonsyl (Boc) protection method and fluorenylmethoxycarbonyl (Fmoc) protection methods/groups. Therefore, whenever an amino acid has been bonded, a deprotection procedure must be executed (i.e., the amino on the solid-phase carrier is deprotected first, and then has a condensation reaction with the carboxyl of the next target amino acid to be bonded among amino acids in excessive quantity, to extend the peptide chain). The process is repeated through such steps, i.e., condensation, washing, deprotection, neutralization, washing, and then next cycle of condensation (for bonding the target amino acid) is executed, till required length of target peptide chain to be synthesized is reached. After the synthesis is finished, the target polypeptide is cleaved from the resin with a TFA method, to obtain a crude product of target peptide.

The purification process is as shown in FIG. 1.

Usually, when a linear-chain polypeptide is synthesized, lysine (Lys, K) Fmoc-Lys(Boc)-OH with one active amino is used, and the amino groups on the side chains are protected by BOC—OH to prevent them from participating in the condensation reaction. Therefore, only one amino group in the lysine (Lys, K) can undergo the condensation reaction, and thereby the amino acids are bonded up one by one, and the peptide chain is extended linearly However, when the branched skeleton described in the present invention is synthesized, the branch point is a lysine Fmoc-Lys(Fmoc)-OH with two active amino groups, and the amino group on the side chain of the lysine also participates in the condensation reaction. Therefore, when the amino-acid condensation reaction proceeds from the lysine (Lys, K), branch chains will be developed, and a branched skeleton ">KY-WANG solid resin" will be formed. When the next cycle of condensation of lysine Fmoc-Lys(Fmoc)-OH is further executed on that basis, a four-branch skeleton ">$K_2$KY-WANG solid resin" will be formed; next, when the condensation of Fmoc-Lys(Fmoc)-OH is continued further, an eight-branch skeleton ">$K_4 K_2$KY-WANG solid resin" will be formed.

In the present invention, the lysine (Lys, K, Fmoc-Lys (Fmoc)-OH) with two active amino groups in KY is used as a branch point, and two amino acids for the next step of the operation are bonded by condensation at the same time. If $X_A X_B X_C X_D X_E\text{-}X$ is bonded, a two-branch peptide molecule $(X_A X_B X_C X_D X_E\text{-}X)_2 KY$ with two copies of $X_A X_B X_C X_D X_E\text{-}X$ will be formed. Or, two K (Fmoc-Lys (Fmoc)-OH) may be bonded first to form a two-branch skeleton, and the two amino acids K for the next step of the operation in "$K_2$" have two active amido groups respectively; thus, a branch point with four active amino groups is formed for condensation of amino acids ($X_A X_B X_C X_D X_E\text{-}X$) in the next step. Through such condensation in the sequence of $X_A X_B X_C X_D X_E\text{-}X$, the peptide chain is extended and a four-branch peptide molecule $\{(X_A X_B X_C X_D X_E\text{-}X)_2 K\}_2 KY$ that contains four copies of $X_A X_B X_C X_D X_E\text{-}X$ is formed. Alternatively, two K (Fmoc-Lys(Fmoc)-OH) may be bonded first to form a two-branch skeleton, and then four K (Fmoc-Lys(Fmoc)-OH) may be bonded to form a four-branch skeleton, and the four amino acids K for the next step of operation in "$K_4$" have two active amino groups respectively; thus, a branch point with eight active amino groups is formed for condensation of amino acids ($X_A X_B X_C X_D X_E$-X) in the next step. Through such condensation in the sequence of $X_A X_B X_C X_D X_E$-X, the peptide chain is extended and an eight-branch peptide molecule $\{(\{X_A X_B X_C X_D X_E$-$X\}_2 K)_2 K\}_2 KY$ that contains eight copies of $X_A X_B X_C X_D X_E$-X is formed. In that way, a multi-branch peptide molecule that contains sixteen copies, thirty-two copies, or more copies of $X_A X_B X_C X_D X_E$-X can be formed.

After the synthesis utilizing the WANG solid resin is finished, the peptide chain can be cleaved from the WANG solid resin with a TFA method, so as to obtain a two-branch, four-branch, or eight-branch peptide molecule, or a peptide molecule with more branches, as described above.

Polypeptide synthesis is a conventional technique presently. Please see Chapter 3 "Chemical Synthesis and Purification of Polypeptides" in the book "Contemporary Theory and Application of Polypeptide Hormones" authored by Shuli Shen and published by Scientific and Technical Documentation Express (in 1998) for the principle and operation of synthesis and purification of polypeptides. The synthesis and preparation of the polypeptide compound in the present invention may be implemented with the above-mentioned solid phase synthesis method, but is not limited to that method.

Hereunder the present invention will be further detailed in embodiments, but those embodiments should not be understood as constituting any limitation to the present invention. Any modification or change made by those skilled in the art to the embodiments in the present invention according to the reveal in this document shall be deemed as falling in the scope of the present invention.

Embodiment 1: Synthesis of a Copy of a Peptide Fragment

The polypeptide compound in the present invention has the same copy of the peptide fragment $X_A X_B X_C X_D X_E$-X, regardless of whether it is in a two-branch, four-branch, or eight-branch structure. In the copy of the peptide fragment, $X_A$ is a polar amino acid molecule, and may be selected from cysteine (Cys, C), glycine (Gly, G), serine (Ser, S), threonine (Thr, T), tyrosine (Tyr, Y), asparagine (Asn, N), or glutamine (Gln, Q); $X_B$ and $X_E$ are alkaline amino acid molecules (the same or different), and may be selected from one or two of arginine (Arg, R), lysine (Lys, K), and histidine (His, H); $X_C$ and $X_D$ are non-polar amino acid molecules (the same or different), and may be selected from one or two of alanine (Ala, A), valine (Val, V), leucine (Leu, L), isoleucine (Ile, I), proline (Pro, P), phenylalanine (Phe, F), tryptophan (Trp, W), and methionine (Met, M); X is null, or any one amino acid, or a peptide fragment composed of any number of amino acids, or a chemical group that can bond with amino acids and peptide fragments. The possible combinations are shown in Table 1-4, but the present invention is not limited to those combinations.

During the synthesis, an amino acid solid-phase synthesis method protected by organic chemical Fmoc protection may be used. The specific operation is as follows:

Step 1: a commercial raw material "X-WANG solid resin" or "$X_E$-WANG solid resin" is selected first, and the amido terminal of X or $X_E$ is protected with an Fmoc protection method;

Step 2: $X_E$ or $X_D$ is selected to condense the amino acids one by one and extend the peptide chain, so as to synthesize an $X_A X_B X_C X_D X_E$-X copy peptide fragment: In this embodiment, the synthesis of the copy peptide fragment is implemented by condensing the amino acids one by one from the carboxyl terminal (C) to the amino terminal (N) of the polypeptide and thereby extending the chain on an automatic polypeptide synthesizer (model AB1433 Å), and then cracking the target polypeptide from the WANG solid resin with a TFA method after the synthesis is finished.

On the automatic polypeptide synthesizer (model AB1433 Å), X or $X_E$ is fixed to the WANG solid resin (the WANG solid resin is a carrier for Fmoc protection in the solid phase peptide synthesis) first, and then amino acids ($X_E$, $X_D$, $X_C$, $X_B$, $X_A$ or $X_D$, $X_C$, $X_B$, $X_A$) are bonded by condensation. The actual bonding sequence is WANG solid resin-X-$X_E X_D X_C X_B X_A$. Thus, a copy peptide fragment fixed to the WANG solid resin is obtained. Finally, the target copy peptide fragment is cracked from the WANG solid resin with a TFA method. Thus, a crude product of the $X_A X_B X_C X_D X_E$-X copy of the peptide fragment is obtained.

Step 3: purification of the $X_A X_B X_C X_D X_E$-X copy of the peptide fragment The crude product is purified with a chromatographic column (model: Daiso C18, 10 µm, 100 Å, 50×250 mm), wherein, the mobile phase A in the chromatographic operation is an aqueous solution that contains 0.05% trifluoroacetic acid and 2% acetonitrile, the mobile phase B is 90% acetonitrile/water, the flow rate is 25 mL/min., and the ultraviolet detection wavelength is 220 nm. The eluting peak solution is collected and then freeze-dried. Thus, white flocculent $X_A X_B X_C X_D X_E$-X copy peptide fragments are obtained. Then, the copy peptide fragments are packed in a sealed state and stored in a refrigerator for later use; the purity of the copy peptide fragments may be >99%.

$X_A$, $X_B$, $X_C$, $X_D$ and $X_E$ are commercially available. When the polypeptide compound in the present invention is prepared, the WANG solid resin-X or WANG solid resin-$X_E$ that is purchased commercially may be also used as a raw material, and amino acids are condensed to the terminal end of X or $X_E$, so as to obtain the copy peptide fragment described in the present invention. Some of the copy peptide fragments obtained through synthesis and their molecular weights measured by mass spectrometer measurement are listed in Table 1.

TABLE 1

List of Groups in the Copy Peptide Fragment $X_A X_B X_C X_D X_E$-X

| Embodiment | $X_A$ | $X_B$ | $X_C$ | $X_D$ | $X_E$ | X | Molecular Weight Theoretical | Molecular Weight Actual |
|---|---|---|---|---|---|---|---|---|
| 1-1 | T | K | L | P | R | Null | 613.75 | 613.98 |
| 1-2 | S | R | P | L | R | G | 684.79 | 684.93 |
| 1-3 | C | R | L | P | R | G | 700.86 | 701.25 |
| 1-4 | T | R | P | L | R | C | 744.91 | 745.18 |
| 1-5 | S | K | L | L | K | G | 644.80 | 645.32 |
| 1-6 | Q | K | A | P | H | Null | 579.65 | 580.04 |
| 1-7 | Y | R | F | M | K | A | 815.01 | 815.53 |
| 1-8 | C | K | L | P | R | Null | 615.79 | 616.24 |

It is seen from the result in Table 1: the deviation of the measured molecular weight of the copy peptide fragment synthesized in the present invention from the theoretical molecular weight is less than 1%, which proves that the copy of the peptide fragment is the correct copy of the peptide fragment in the corresponding embodiment.

This embodiment part is provided to disclose the content of the copy peptide fragment, rather than limit the present invention. The actual synthesis may be executed according to the description in the following embodiments.

A branched skeleton is prepared with the method described in the present invention, wherein, the amino acid at the branch node is Fmoc-Lys(Fmoc)-OH that carries two active amino groups, which provide a branch loci for the subsequent amino-acid condensation and bonding reactions. Therefore, a two-branch skeleton ">KY-WANG solid resin", four-branch skeleton ">$K_2$KY-WANG solid resin", or eight-branch skeleton ">$K_4K_2$KY-WANG solid resin", . . . , can be synthesized. Then, amino acids in which the amino groups are protected are selected according to the conventional peptide extension reaction, and peptide extension from the branch nodes is executed, so as to prepare the two-branch peptide molecule $(X_AX_BX_CX_DX_E-X)_2$KY, four-branch peptide molecule $\{(X_AX_BX_CX_DX_E-X)_2K\}_2$KY, or eight-branch peptide molecule $\{(\{X_AX_BX_CX_DX_E-X\}_2K)_2K\}_2$KY of the present invention. In view of the peptide chain extension process being a mature technique, the details of the synthesis steps will not be described any further here.

Embodiment 2: Synthesis of a Two-Branch Peptide Molecule $(X_AX_BX_CX_DX_E-X)_2$KY The structure and synthesis route of the polypeptide compound $(X_AX_BX_CX_DX_E-X)_2$KY with two copies of $X_AX_BX_CX_DX_E$-X provided in the present invention are shown in formula 1, wherein, $X_A$ is a polar amino acid molecule, $X_B$ and $X_E$ are alkaline amino acid molecules, $X_C$ and $X_D$ are non-polar amino acid molecules, K is lysine Fmoc-Lys(Fmoc)-OH that contains two active amino groups, and X and Y are null, or any one or more amino acids or chemical groups:

formula (1)

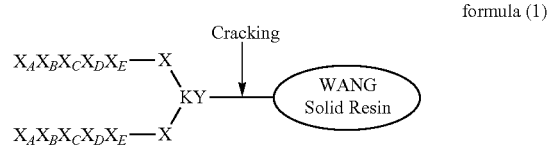

In this embodiment, an amino acid solid-phase synthesis method protected by an organic chemical Fmoc protection method is used. The specific operation is as follows:
Step 1: The amido groups of the lysine are protected with an Fmoc protection method;
Step 2: The $(X_AX_BX_CX_DX_E-X)_2$KY polypeptide compound is synthesized: In this embodiment, the synthesis of the polypeptide is implemented by condensing the amino acids one by one from the carboxyl terminal (C) to the amino terminal (N) of the polypeptide and thereby extending the chain on an automatic polypeptide synthesizer (model ABI433 Å), and then cracking the target polypeptide from the WANG solid resin with a TFA method after the synthesis is finished.

On the automatic polypeptide synthesizer (model AB1433 Å), Y is fixed to the WANG solid resin (the WANG solid resin is a carrier for Fmoc protection in the solid phase peptide synthesis) first, and then lysine (Fmoc-Lys(Fmoc)-OH) is bonded by condensation. The actual bonding sequence is WANG solid resin-Y-Lys. Thus, a two-branch skeleton ">KY-WANG solid resin" with branch nodes is formed; since the terminal lysine has two activated amino groups, the two active amino terminals of K in the ">KY-WANG solid resin" will react with another two $X_AX_BX_CX_DX_E$-X segments. Thus, an extended two-branch peptide $(X_AX_BX_CX_DX_E-X)_2$Y-WANG solid resin is obtained, i.e., a polypeptide compound $(X_AX_BX_CX_DX_E-X)_2$KY-WANG solid resin with two copies of $X_AX_BX_CX_DX_E$-X, which are fixed to the WANG solid resin, is obtained.

In this step, $X_AX_BX_CX_DX_E$-X segments may be synthesized as described in embodiment 1 first, and then they may be condensed with the WANG solid resin-Y-Lys; or, the two active amino terminals of K in the ">KY-WANG solid resin" may be bonded with X, $X_E$, $X_D$, $X_C$, $X_B$ and $X_A$ in sequence. Finally, the target polypeptide compound may be cracked from the WANG solid resin with a TFA method, to obtain a crude product of a $(X_AX_BX_CX_DX_E-X)_2$KY polypeptide compound.

Step 3: purification of $(X_AX_BX_CX_DX_E-X)_2$KY polypeptide compound

The crude product is purified using a chromatographic column (model: Daiso C18, μm, 100 Å, 50×250 mm), wherein, the mobile phase A in the chromatographic operation is an aqueous solution that contains 0.05% trifluoroacetic acid and 2% acetonitrile, the mobile phase B is 90% acetonitrile/water, the flow rate is 25 mL/min., and the ultraviolet detection wavelength is 220 nm. The eluting peak solution is collected and then freeze-dried. Thus, a white flocculent $(X_AX_BX_CX_DX_E-X)_2$KY polypeptide compound is obtained. Then, the polypeptide compound is packed in a sealed state and stored in a refrigerator for later use; the purity of the polypeptide compound may be >99%.

$X_A$, $X_B$, $X_C$, $X_D$ and $X_E$ are commercially available. When the polypeptide compound in the present invention is prepared, the WANG solid resin-Y that is purchased commercially may also be used as a raw material, and the amino acids may be condensed to the terminal portions of Y with the above-mentioned method, so as to obtain the polypeptide compound in the present invention.

A series of two-branch peptide molecules $(X_AX_BX_CX_DX_E-X)_2$KY are obtained with the method described in this embodiment, and are shown in Table 2.

TABLE 2

List of Groups in the Two-Branch Peptide Molecule $(X_AX_BX_CX_DX_E-X)_2$KY

| Embodiment | $X_A$ | $X_B$ | $X_C$ | $X_D$ | $X_E$ | X | Y |
|---|---|---|---|---|---|---|---|
| 2-1 | T | K | L | P | R | Null | G |
| 2-2 | S | R | P | L | R | G | A |
| 2-3 | C | R | L | P | R | G | G |
| 2-4 | T | R | P | L | R | C | G |
| 2-5 | S | K | L | L | K | G | Null |
| 2-6 | Q | K | A | P | H | Null | G |
| 2-7 | Y | R | F | M | K | A | C |
| 2-8 | C | K | W | A | H | Null | A |
| 2-9 | S | K | L | I | K | Null | G |
| 2-10 | C | R | L | A | K | A | Null |
| 2-11 | S | R | L | F | R | G | W |
| 2-12 | T | K | P | P | R | Null | G |
| 2-13 | T | R | P | L | K | Null | G |
| 2-14 | S | K | I | L | R | Null | G |
| 2-15 | C | H | V | M | K | P | I |
| 2-16 | N | H | L | W | H | N | D |

Embodiment 3: Synthesis of a Four-Branch Peptide Molecule $\{(X_AX_BX_CX_DX_E-X)_2K\}_2$KY The structure and synthesis route of the polypeptide compound $\{(X_AX_BX_CX_DX_E-X)_2K\}_2$KY with four copies of $X_AX_BX_CX_DX_E$-X as provided in the present invention are shown in formula 2.

The structure may also be expressed as $(X_AX_BX_CX_DX_E-X)_4K_2$KY. The definitions of the groups are the same as those in the embodiment 2:

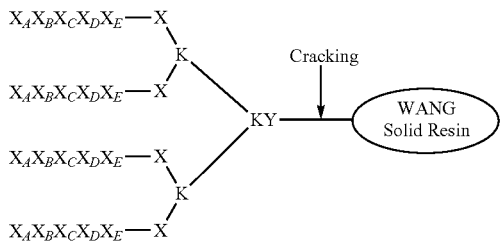

formula (2)

In this embodiment, an amino acid solid-phase synthesis method protected by an organic chemical Fmoc protection method is used. The specific operation is as follows:
Step 1: The amido groups of the lysine are protected with an Fmoc protection method;
Step 2: The $\{(X_AX_BX_CX_DX_E\text{-}X)_2K\}_2KY$ polypeptide compound is synthesized:

In this embodiment, the synthesis of the polypeptide is implemented by condensing the amino acids one by one from the carboxyl terminal (C) to the amino terminal (N) of the polypeptide and thereby extending the chain on an automatic polypeptide synthesizer (model ABI433 Å), and then cracking the target polypeptide from the WANG solid resin with a TFA method after the synthesis is finished.

On the automatic polypeptide synthesizer (model AB1433 Å), Y is fixed to the WANG solid resin (the WANG solid resin is a carrier for Fmoc protection in the solid phase peptide synthesis) first, and then lysine (Fmoc-Lys(Fmoc)-OH) is bonded by condensation. The actual bonding sequence is WANG solid resin-Y-Lys. Thus, a two-branch skeleton ">KY-WANG solid resin" with branch nodes is formed; since the terminal lysine has two activated amino groups, the two activated amino groups will undergo a condensation reaction with the carboxyl terminals of another two lysines (K, here, the two amino groups are protected). Thus, two extended branch skeletons of the $K_2$KY-WANG solid resin are obtained. Here, the amino terminals of the lysine in KY are bonded with two lysines (K), each of which has two active amino groups; thus, a four-branch skeleton ">$K_2$KY-WANG solid resin" with branch nodes is formed; the condensation with two $X_AX_BX_CX_DX_E$-X segments is executed further on each lysine (K) that has two active amino groups in "$K_2$"; thus, a polypeptide compound $\{(X_AX_BX_CX_DX_E\text{-}X)_2K\}_2$KY-WANG solid resin with four copies of $X_AX_BX_CX_DX_E$-X, which is fixed to the WANG solid resin, is obtained.

In this step, $X_AX_BX_CX_DX_E$-X segments may be synthesized as described in embodiment 1, and then they may be condensed with the $K_2$KY-WANG solid resin; or, the two active amino terminals of K in the ">$K_2$KY-WANG solid resin" may be bonded with X, $X_E$, $X_D$, $X_C$, $X_B$ and $X_A$ in sequence. Finally, the target polypeptide compound may be cracked from the WANG solid resin with a TFA method, to obtain a crude product of $\{(X_AX_BX_CX_DX_E\text{-}X)_2K\}_2$KY polypeptide compound.

Step 3: purification of $\{(X_AX_BX_CX_DX_E\text{-}X)_2K\}_2$KY polypeptide compound The purification is the same as that in the embodiment 2. Finally, a white flocculent $\{(X_AX_BX_CX_DX_E\text{-}X)_2K\}_2$KY polypeptide compound is obtained. Then, the polypeptide compound is packed in a sealed state and stored in a refrigerator for later use; the purity of the polypeptide compound may be >99%.

A series of four-branch peptide molecules $\{(X_AX_BX_CX_DX_E\text{-}X)_2K\}_2$KY are obtained using the method described in this embodiment. Please see Table 3 for the selection of the groups.

TABLE 3

List of Groups in the Four-Branch Peptide Molecule $\{(X_AX_BX_CX_DX_E\text{-}X)_2K\}_2$KY

| Embodiment | $X_A$ | $X_B$ | $X_C$ | $X_D$ | $X_E$ | X | Y |
|---|---|---|---|---|---|---|---|
| 4-1 | T | K | L | P | R | Null | G |
| 4-2 | S | R | P | L | R | G | A |
| 4-3 | C | R | L | P | R | G | G |
| 4-4 | T | R | P | L | R | Null | G |
| 4-5 | S | K | L | L | K | G | Null |
| 4-6 | Q | K | A | P | H | Null | G |
| 4-7 | Y | R | F | M | K | A | C |
| 4-8 | C | K | W | A | H | Null | A |
| 4-9 | S | K | L | I | K | Null | G |
| 4-10 | C | R | L | A | K | A | Null |
| 4-11 | S | R | L | F | R | G | W |
| 4-12 | T | K | P | P | R | Null | G |
| 4-13 | T | R | P | L | K | Null | G |
| 4-14 | S | K | I | L | R | Null | G |
| 4-15 | C | H | V | M | K | P | I |
| 4-16 | N | H | L | W | H | N | D |

Embodiment 4: Synthesis of Eight-Branch Peptide Molecule $\{(\{X_AX_BX_CX_DX_E\text{-}X\}_2K)_2K\}_2$KY The structure and synthesis route of the polypeptide compound $\{(\{X_AX_BX_CX_DX_E\text{-}X\}_2K)_2K\}_2$KY with eight copies of $X_AX_BX_CX_DX_E$-X provided in the present invention are shown in formula 3. The structure may also expressed as $(X_AX_BX_CX_DX_E\text{-}X)_8K_4K_2$KY. The definitions of the groups are the same as those in embodiment 2:

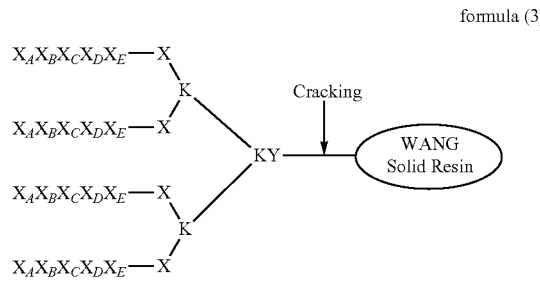

formula (3)

In this embodiment, an amino acid solid-phase synthesis method protected by an organic chemical Fmoc protection method is used. The specific operation is as follows:
Step 1: The amino groups of the lysine are protected with an Fmoc protection method;
Step 2: synthesis of $\{(\{X_AX_BX_CX_DX_E\text{-}X\}_2K)_2K\}_2$KY polypeptide compound:

In this embodiment, the synthesis of the polypeptide is implemented by condensing the amino acids one by one from the carboxyl terminal (C) to the amino terminal (N) of the polypeptide and thereby extending the chain on an automatic polypeptide synthesizer (model ABI433 Å), and then cracking the target polypeptide from the WANG solid resin with a TFA method after the synthesis is finished.

On the automatic polypeptide synthesizer (model ABI433 Å), Y is fixed to the WANG solid resin (the WANG solid resin is a carrier for Fmoc protection in the solid phase peptide synthesis) first, and then lysine (Lys, K) is bonded by condensation. The actual bonding sequence is WANG solid resin-Y-Lys. Thus, a two-branch skeleton ">KY-WANG solid resin" with branch nodes is formed; since the terminal lysine has two activated amino groups, the two activated amino groups will have a condensation reaction with the carboxyl terminals of another two lysines (K, here, the two amino groups are protected). Thus, two extended branch skeletons $K_2$KY-WANG solid resin are obtained. Here, the amino terminals of the lysine in KY are bonded with two lysines (K, here, the two amino groups are protected), each of which has two active amino groups; thus, a four-branch skeleton ">$K_2$KY-WANG solid resin" with branch nodes is formed; the terminal ends of two lysines that have a single activated amino group each in "$K_2$" have a condensation reaction with the carboxyl terminals of another two lysines (K, here, the two amino groups are protected). Thus, extended four-branch skeletons of the $K_4K_2$KY-WANG solid resin are obtained. Here, the amino terminals of the terminal lysine in $K_2$KY are bonded with four lysines (K), each of which has two active amino groups; thus, an eight-branch skeleton ">$K_4K_2$KY-WANG solid resin" with branch nodes is formed; the condensation with two $X_AX_BX_CX_DX_E$-X segments is executed further on each lysine (K) that has two active amino groups in "$K_4$" in the "$K_4K_2$KY-WANG solid resin"; thus, a polypeptide compound $\{(\{X_AX_BX_CX_DX_E\text{-}X\}_2K)_2K\}_2$KY-WANG solid resin with eight copies of $X_AX_BX_CX_DX_E$-X, which is fixed to the WANG solid resin, is obtained.

In this step, the $X_AX_BX_CX_DX_E$-X segments may be synthesized first, and then they may be condensed with the $\{(K)_2K\}_2$KY-WANG solid resin; or, the two active amino terminals of K in the ">$K_4K_2$KY-WANG solid resin" may be bonded with X, $X_E$, $X_D$, $X_C$, $X_B$ and $X_A$ in sequence. Finally, the target polypeptide compound may be cracked from the WANG solid resin with a TFA method, to obtain a crude product of $\{(\{X_AX_BX_CX_DX_E\text{-}X\}_2K)_2K\}_2$KY polypeptide compound.

Step 3: purification of $\{(\{X_AX_BX_CX_DX_E\text{-}X\}_2K)_2K\}_2$KY polypeptide compound The purification is the same as that in embodiment 2. Finally, a white flocculent $\{(\{X_AX_BX_CX_DX_E\text{-}X\}_2K)_2K\}_2$KY polypeptide compound is obtained. Then, the polypeptide compound is packed in a sealed state and stored in a refrigerator for later use; the purity of the polypeptide compound may be >99%.

A series of eight-branch peptide molecules $\{(\{X_AX_BX_CX_DX_E\text{-}X\}_2K)_2K\}_2$KY are obtained with the method described in this embodiment. Please see Table 4 for the selection of the groups.

TABLE 4

List of Groups in the Eight-Branch Peptide Molecule $\{(\{X_AX_BX_CX_DX_E\text{-}X\}_2K)_2K\}_2$KY

| Embodiment | $X_A$ | $X_B$ | $X_C$ | $X_D$ | $X_E$ | X | Y |
|---|---|---|---|---|---|---|---|
| 8-1 | T | K | L | P | R | Null | G |
| 8-2 | S | R | P | L | R | G | A |
| 8-3 | C | R | L | P | R | G | G |
| 8-4 | T | R | P | L | R | Null | G |
| 8-5 | S | K | L | L | K | G | Null |
| 8-6 | Q | K | A | P | H | Null | G |
| 8-7 | Y | R | F | M | K | A | C |
| 8-8 | C | K | W | A | H | Null | A |
| 8-9 | S | K | L | I | K | Null | G |
| 8-10 | C | R | L | A | K | A | Null |
| 8-11 | S | R | L | F | R | G | W |
| 8-12 | T | K | P | P | R | Null | G |

TABLE 4-continued

List of Groups in the Eight-Branch Peptide Molecule $\{(\{X_AX_BX_CX_DX_E\text{-}X\}_2K)_2K\}_2$KY

| Embodiment | $X_A$ | $X_B$ | $X_C$ | $X_D$ | $X_E$ | X | Y |
|---|---|---|---|---|---|---|---|
| 8-13 | T | R | P | L | K | Null | G |
| 8-14 | S | K | I | L | R | Null | G |
| 8-15 | C | H | V | M | K | P | I |
| 8-16 | N | H | L | W | H | N | D |

Since the polypeptide compound in the present invention is a type of organic molecule with biological activity, their biological effects depend on their amino acid sequence and structure. Any change of a single amino acid in the protein or peptide sequence may result in changes of the biological activity. Hereunder the biological activity and efficacy of the polypeptide compound provided in the present invention will be described in specific experimental examples.

Experimental Example 1: Experiment of the Immune Effect of the Polypeptide Compound Provided in the Present Invention Among Birds and Poultry (Chicks)

Newcastle Disease Virus (NDV) can cause a hemagglutination phenomenon among chickens, which is a specific antibody neutralization reaction. The principle is that the hemagglutinin produced by the virus can cause agglutination of red blood cells. However, if a specific antibody is used to counteract the virus first before the virus is added into red blood cells, the hemagglutination phenomenon will not occur any more. Such a test is referred to as a Hemagglutination inhibition test (HI), and the maximum multiple of dilution of the anti-serum used in the detection is the titer of the antibody. The higher the titer of the tested antibody, the better the immune effect is.

The HI method has the following advantages:
1. High sensitivity: the HI method can detect antibody in a trace quantity, and the result is relatively accurate, the reaction is one of sensitive serologic detection reactions;
2. High specificity: the virus that causes agglutination of red blood cells can only be inhibited by a specific antibody;
3. High detection speed: only about 2 h is required in a HI test to judge the result;
4. The HI test doesn't have any high requirement for the environment, and the operation is simple and quick, a large quantity of samples can be detected in one test.

The polypeptide compounds obtained in the embodiments 2-1~2-16, 4-1~4-16, and 8-1~8-16 in the present invention are used for testing of the antibody titer among chicks: Live NDV vaccine (CS2 strain, from Chengdu Tecbond Biological Products Co., Ltd.) and the polypeptide compound provided in the present invention are inoculated into SPF chicks, and then the HI antibody formation effect of the polypeptide compound against live NDV vaccine in the bodies of SPF chicks is tested, so as to ascertain the immune effect of the polypeptide compound provided in the present invention against live NDV vaccine (antigen).

The experimental method is as follows: 7-day-old specific pathogen free chicks (abbreviated as SPF chicks) are chosen. The SPF chicks are divided into 8 groups, with 12 chicks in each group. Subcutaneous vaccination is carried out in the axillary region of a wing of each SPF chick in the following groups. The SPF chicks in each group are bred in isolators. About 1 ml venous blood is taken under a wing of each SPF chick on the fourteenth day after inoculation, the serum is separated, and the HI detection is carried out. The detection results of the embodiments 2-5, 2-6, 4-9, 4-12, 8-13 and 8-14 (corresponding to the experimental groups 1-6 sequentially) are shown in Table 5 (only a part of the detection results of the polypeptide compounds are listed). The results of the other embodiments have little difference with those shown in Table 5, and are omitted here. See the "Experiment Course of Animal Immunology" authored by Xin Guo and published by the Press of China Agricultural University in 2007 for the details of operation.

Blank group: 0.3 ml normal saline is injected;

Reference group: 0.3 ml live NDV vaccine (abbreviated as "vaccine", CS2 strain) is inoculated;

Experimental group: 0.3 ml vaccine mixed with 0.2 μg polypeptide compound provided in the present invention is inoculated.

TABLE 5

Result of Immunity Experiment of SPF Chicks

| Group | Inoculated Substance | | Average Antibody Titer |
|---|---|---|---|
| | Vaccine | Embodiment | |
| Blank group | None | None | Negative |
| Reference group | Vaccine | None | 8.3log2 |
| Experimental group 1 | Vaccine | 2-5 | 9.3log2 |
| Experimental group 2 | Vaccine | 2-6 | 9.4log2 |
| Experimental group 3 | Vaccine | 4-9 | 9.7log2 |
| Experimental group 4 | Vaccine | 4-12 | 9.8log2 |
| Experimental group 5 | Vaccine | 8-13 | 10.0log2 |
| Experimental group 6 | Vaccine | 8-14 | 10.2log2 |

Note:
"Negative" refers to that the HI antibody titer is zero;

The dietetic activities of the SPF chicks in the groups are normal during the experiment, no adverse reaction is seen, and no SPF chick dies. That indicates the polypeptide compound provided in the present invention is safe to use. The results in Table 5 indicate that the average HI antibody titer (experimental groups 1-8) is higher after the polypeptide compound provided in the present invention is added, when compared with the blank group and reference group (vaccine is inoculated solely). Thus, it is proved that a good immunity enhancement effect can be attained when the polypeptide compound provided by the present invention is used in combination with the vaccine, and the average HI antibody titer is higher than that of the reference by 1 or more.

Experimental Example 2: Experiment on the Influence of Different Branches of the Polypeptide Compound Provided in the Present Invention on the Immune Effect Under a Condition of the Same Multi-Copy Group An experiment on the immune effect of two groups of polypeptide compounds (groups I and II) in the present invention is carried out with the method described in the experimental example 1. In the two groups of polypeptide compounds, the multi-copy groups of the polypeptide compounds in the same group are the same, only the quantities of branches are different. The two groups of compounds are selected randomly from the embodiments. The detection results of the embodiments 2-1, 2-3, 4-1, 4-3, 8-1 and 8-3 are shown in Table 6. The results of the other embodiments have little difference from those shown in Table 5, and are omitted here.

Group division:

Blank group: 0.3 ml normal saline is injected;

Reference group: 0.3 ml live NDV vaccine (abbreviated as "vaccine", CS2 strain) is inoculated;

Experimental group: in the embodiments, 0.3 ml vaccine mixed with 0.2 μg polypeptide compounds is inoculated;

TABLE 6

Result of Immunity Experiment of SPF Chicks

| Group | | Inoculated Substance | | Average Antibody Titer |
|---|---|---|---|---|
| | | Vaccine | Embodiment | |
| Blank group | | None | None | Negative |
| Reference group | | Vaccine | None | 8.3log2 |
| Experimental group | Group I | Vaccine | 2-1 | 9.4log2 |
| | | Vaccine | 4-1 | 9.7log2 |
| | | Vaccine | 8-1 | 10.2log2 |
| | Group II | Vaccine | 2-3 | 9.5log2 |
| | | Vaccine | 4-3 | 9.9log2 |
| | | Vaccine | 8-3 | 10.3log2 |

Note:
"Negative" refers to that the HI antibody titer is zero.

The dietetic activities of the SPF chicks in the groups are normal during the experiment. No adverse reaction is seen, and no SPF chick dies. That indicates the polypeptide compound provided in the present invention is safe to use.

The results in Table 6 indicates that the immune response effect to the chicks is improved and the immune enhancement effect is further improved as the number of copies of the polypeptide segment is increased (i.e., the quantity of branches is increased). That means the biological effect is positively correlated to the number of copies of the peptide fragments.

INDUSTRIAL APPLICABILITY

The polypeptide compounds provided in the present invention are useful effective ingredients in a variety of medicines, and are applicable to medicines for preventing and treating many diseases. Especially, the polypeptide compounds can be used to prepare medicines for enhancing immune ability, and are suitable for industrial application.

I claim:

1. A polypeptide compound, having a structural formula expressed as $(X_AX_BX_CX_DX_E-X)_2KY$, $\{(X_AX_BX_CX_DX_E-X)_2K\}_2KY$ or $\{(\{X_AX_BX_CX_DX_E-X\}_2K)_2K\}_2KY$;

wherein, $X_A$ is a polar amino acid molecule, $X_B$ and $X_E$ are alkaline amino acid molecules (the same or different), $X_C$ and $X_D$ are non-polar amino acid molecules (the same or different), K is lysine (Lys, K), and X and Y are null, or one or more of amino acid or chemical groups, wherein the $\{(X_AX_BX_CX_DX_E-X)_2K\}_2KY$ structure is shown in formula 5:

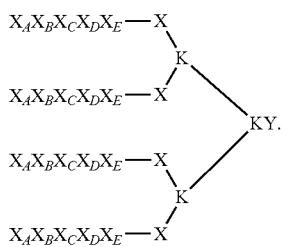

formula 5

2. The polypeptide compound according to claim 1, wherein, the $(X_AX_BX_CX_DX_E\text{-}X)_2KY$ structure is shown in formula 4:

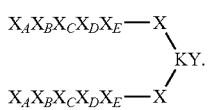

formula 4

3. The polypeptide compound according to claim 1, wherein, the $\{(\{X_AX_BX_CX_DX_E\text{-}X\}_2K)_2K\}_2KY$ structure is shown in formula 6:

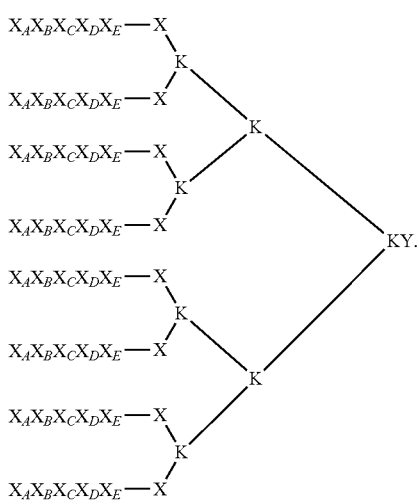

formula 6

4. The polypeptide compound according to claim 1, wherein, X and Y are null, or any amino acid, or peptide fragments composed of any number of amino acids, or chemical groups that can connect amino acids or peptide fragments, and X and Y may be the same or different from each other.

5. The polypeptide compound according to claim 1, wherein, $X_A$ is selected from cysteine (Cys, C), glycine (Gly, G), serine (Ser, S), threonine (Thr, T), tyrosine (Tyr, Y), asparagine (Asn, N), or glutamine (Gln, Q); or $X_A$ is selected from cysteine (Cys, C), serine (Ser, S), threonine (Thr, T), tyrosine (Tyr, Y), asparagine (Asn, N), or glutamine (Gln, Q); or $X_A$ is selected from cysteine (Cys, C), serine (Ser, S), threonine (Thr, T), or glutamine (Gln, Q).

6. The polypeptide compound according to claim 1, wherein, $X_B$ and $X_E$ are selected from arginine (Arg, R), lysine (Lys, K), or histidine (His, H) respectively, and may be the same or different from each other; or $X_B$ is selected from arginine (Arg, R) or lysine (Lys, K).

7. The polypeptide compound according to claim 1, wherein, $X_C$ and $X_D$ are selected from alanine (Ala, A), valine (Val, V), leucine (Leu, L), isoleucine (Ile, I), proline (Pro, P), phenylalanine (Phe, F), tryptophan (Trp, W), or methionine (Met, M) respectively, and may be the same or different from each other; or $X_C$ is selected from alanine (Ala, A), valine (Val, V), leucine (Leu, L), isoleucine (Ile, I), proline (Pro, P), phenylalanine (Phe, F), or tryptophan (Trp, W) and $X_D$ is selected from leucine (Leu, L), isoleucine (Ile, I) or proline (Pro, P).

8. The polypeptide compound of claim 7 wherein $X_C$ is selected from alanine (Ala, A), leucine (Leu, L), isoleucine (Ile, I) or proline (Pro, P); and $X_D$ is selected from leucine (Leu, L), isoleucine (Ile, I) or proline (Pro, P).

9. The polypeptide compound according to claim 1, further comprising a salt compound formed by the polypeptide compound with an organic acid or inorganic acid.

10. The polypeptide compound according to claim 1, further comprising an ether, ester, glucoside, or glycoside compound, formed by the hydroxyl group included in the polypeptide compound.

11. The polypeptide compound according to claim 3, further comprising a thioether or thioglycoside compound, formed by the sulfhydryl group included in the polypeptide compound, or further comprising a compound containing disulfide bonds, which may be formed by the sulfhydryl groups included in the polypeptide compound with cysteine or a peptide containing cysteine.

12. The polypeptide compound according to claim 1, further comprising an acylate or alkylate compound, formed by the amino groups included in the polypeptide compound, or further comprising a glucoside compound formed by the amino group included in the polypeptide compound with saccharides.

13. The polypeptide compound according to claim 1, further comprising an ester or amide compound formed by a carboxyl group included in the polypeptide compound.

14. The polypeptide compound according to claim 1, further comprising a glucoside, acylate, or alkylate compound formed by an imino group included in the polypeptide compound.

15. The polypeptide compound according to claim 1, further comprising an ester, ether, glucoside, or glycoside compound formed by a phenolic hydroxyl group included in the polypeptide compound, or further comprising a salt compound formed by a phenolic hydroxyl group included in the polypeptide compound with organic alkali or inorganic alkali compounds.

16. The polypeptide compound according to claim 3, further comprising a coordinate, clathrate, or chelate compound formed by the polypeptide compound with metal ions.

17. The polypeptide compound according to claim 1, further comprising a hydrate or solvent formed by the polypeptide compound.

18. A pharmaceutical composition comprising the polypeptide compound according to claim 1, a geometrical isomer of the polypeptide compound, or a pharmaceutically acceptable salt of the polypeptide compound, and a pharmaceutical carrier or excipient.

19. An anti-infection or anti-virus medicine for humans or animals comprising a polypeptide compound according to claim 1.

20. A method for preparing the polypeptide compound according to claim 1, wherein, a synthesis route of $(X_AX_BX_CX_DX_E\text{-}X)_2KY$ is expressed by formula 1:

formula (1)

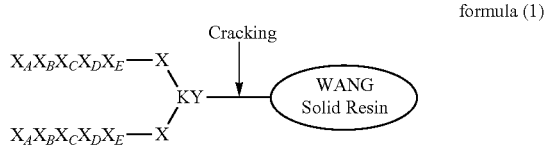

Y is first fixed to a WANG solid resin, and then is bonded with lysine Fmoc-Lys(Fmoc)-OH(Lys, K) by condensation, to form a two-branch skeleton ">KY-WANG solid resin" with branch nodes;

next, the two active terminal amino groups of K in the ">KY-WANG solid resin" are bonded with a $X_AX_BX_CX_DX_E$-X segment respectively, to form a two-branch peptide $(X_AX_BX_CX_DX_E$-X$)_2$KY-WANG solid resin; or the two active terminal amino groups of K in the ">KY-WANG solid resin" are bonded with amino acids X, $X_E$, $X_D$, $X_C$, $X_B$, and $X_A$ by condensation in sequence, to obtain a $(X_AX_BX_CX_DX_E$-X$)_2$KY-WANG solid resin;

Finally, the two-branch peptide is cracked from the WANG solid resin and then purified, to obtain a polypeptide compound $(X_AX_BX_CX_DX_E$-X$)_2$KY with two copies of $X_AX_BX_CX_DX_E$-X.

21. A method for preparing the polypeptide compound according to claim 1, wherein, a synthesis route of the $\{(X_AX_BX_CX_DX_E$-X$)_2$K$\}_2$KY structure is expressed by formula 2:

formula (2)

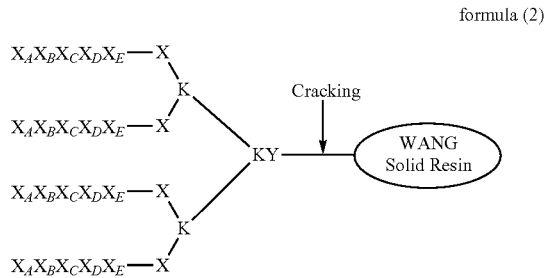

Y is fixed to WANG solid resin first, and then is bonded with lysine Fmoc-Lys(Fmoc)-OH by condensation, to form a two-branch skeleton ">KY-WANG solid resin" with branch nodes; then, the two active terminal amino groups of K in the ">KY-WANG solid resin" are bonded with the terminal carboxyl groups of lysine Fmoc-Lys(Fmoc)-OH by condensation, to form a four-branch skeleton ">K$_2$KY-WANG solid resin" with two branch nodes;

next, the two active terminal amino groups of each lysine K in the ">K$_2$KY-WANG solid resin" are bonded with a $X_AX_BX_CX_DX_E$-X segment respectively, to form a four-branch peptide $(X_AX_BX_CX_DX_E$-X$)_2$KY-WANG solid resin; or the two active terminal amino groups of K in the ">K$_2$KY-WANG solid resin" are bonded with amino acids X, $X_E$, $X_D$, $X_C$, $X_B$, and $X_A$ by condensation in sequence, to obtain a $(X_AX_BX_CX_DX_E$-X$)_4$K$_2$KY-WANG solid resin;

finally, the four-branch peptide is cracked from the WANG solid resin and is purified, to obtain a polypeptide compound $\{(X_AX_BX_CX_DX_E$-X$)_2$K$\}_2$KY with four copies of $X_AX_BX_CX_DX_E$-X.

22. A method for preparing the polypeptide compound according to claim 1, wherein, a synthesis route of the $\{(\{X_AX_BX_CX_DX_E$-X$\}_2$K$)_2$K$\}_2$KY structure is expressed by formula 3:

formula (3)

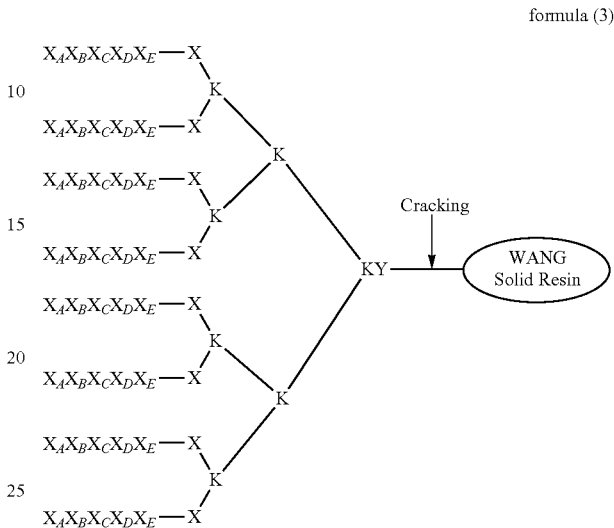

Y is fixed to WANG solid resin first, and then is bonded with lysine Fmoc-Lys(Fmoc)-OH by condensation, to form a two-branch skeleton ">KY-WANG solid resin" with branch nodes; the two active terminal amino groups of K are bonded with the carboxyl terminals of lysine Fmoc-Lys(Fmoc)-OH by condensation, to form a four-branch skeleton "K$_2$KY-WANG solid resin"; then, the two active terminal amino groups of K in the four-branch skeleton ">K$_2$KY-WANG solid resin" are bonded with the terminal carboxyl groups of lysine Fmoc-Lys(Fmoc)-OH by condensation, to form an eight-branch skeleton ">K$_4$K$_2$KY-WANG solid resin" with four branch nodes;

next, the two active terminal amino groups of each lysine K in the ">K$_4$K$_2$KY-WANG solid resin" are bonded with a $X_AX_BX_CX_DX_E$-X segment respectively, to form eight-branch peptide $(X_AX_BX_CX_DX_E$-X$)_8$K$_4$K$_2$KY-WANG solid resin; or the two active terminal amino groups of K in the ">K$_4$K$_2$KY-WANG solid resin" are bonded with amino acids X, $X_E$, $X_D$, $X_C$, $X_B$, and $X_A$ by condensation in sequence, to obtain $(X_AX_BX_C X_DX_E$-X$)_8$K$_4$K$_2$KY-WANG solid resin;

finally, the eight-branch peptide is cracked from the WANG solid resin and purified, to obtain a polypeptide compound $\{(\{X_AX_BX_CX_DX_E$-X$\}_2$K$)_2$K$\}_2$KY with eight copies of $X_AX_BX_CX_DX_E$-X.

23. The method according to claim 20, wherein, before the carboxyl terminal of K is condensed with Y-WANG solid resin, the two amino groups of K are protected with the t-butyloxycarbonyl (Boc) protection method or with the fluorenylmethoxycarbonyl (Fmoc) protection method.

24. The method according to claim 20, wherein, before the carboxyl terminals of the other two lysines are condensed with the two terminal amido groups of K in KY, the two amido groups of each lysine are protected; before the carboxyl terminal of the $X_AX_BX_CX_DX_E$-X is condensed with the terminal amido group of each lysine, the amino group of the $X_AX_BX_CX_DX_E$-X is protected with the t-butyloxycarbonyl (Boc) protection method or with the fluorenylmethoxycarbonyl (Fmoc) protection method.

25. The method according to claim 20, comprising the following steps:
- step 1: protecting the two amino groups of the lysine K with an Fmoc protection method;
- step 2: fixing KY to the WANG solid resin with an automatic polypeptide synthesizer, in the following bonding sequence: WANG solid resin-YK;
  - when the two-copy polypeptide compound is prepared, the two activated terminal amino groups of lysine in KY are further condensed with another two $X_AX_BX_CX_DX_E$-X fragments, to obtain the polypeptide compound $(X_AX_BX_CX_DX_E\text{-}X)_2KY$ with two copies of $X_AX_BX_CX_DX_E$-X, which is fixed to the WANG solid resin; or the two activated terminal amino groups of the lysine in KY are further condensed with another two lysines K, in each of which the two amido groups have been protected with an Fmoc protection method, to obtain a two-branch skeleton $K_2$KY-WANG solid resin;
  - when the four-copy polypeptide compound is prepared, the two activated terminal amino groups of each lysine in the two-branch skeleton "$K_2$" are further condensed with two $X_AX_BX_CX_DX_E$-X fragments, to obtain the polypeptide compound $\{(X_AX_BX_CX_DX_E\text{-}X)_2K\}_2KY$ with four copies of $X_AX_BX_CX_DX_E$-X, which is fixed to the WANG solid resin; or the two activated terminal amino groups of each lysine in the two-branch skeleton "$K_2$" are further condensed with another two lysines K, in each of which the two amino groups have been protected with an Fmoc protection method, to obtain a four-branch skeleton $K_4K_2$KY-WANG solid resin; or
  - when the eight-copy polypeptide compound is prepared, the two activated terminal amino groups of each lysine in the four-branch skeleton "$K_4$" are further condensed with two $X_AX_BX_CX_DX_E$-X fragments, to obtain the polypeptide compound $\{(\{X_AX_BX_CX_DX_E\text{-}X\}_2K)_2K\}_2KY$ with eight copies of $X_AX_BX_CX_DX_E$-X, which is fixed to the WANG solid resin;
- where, the polypeptide compound is cracked from the WANG solid resin with a TFA method, to obtain a crude polypeptide compound product;
- step 3: the crude polypeptide compound product is purified with a chromatographic column (model: Daiso C18, 10 μm, 100 Å, 50×250 mm), wherein, the mobile phase A is an aqueous solution that contains 0.05% trifluoroacetic acid and 2% acetonitrile, the mobile phase B is 90% acetonitrile/water, the flow rate is 25 mL/min., and the ultraviolet detection wavelength is 220 nm; the eluting peak solution is collected and then freeze-dried, to obtain a white flocculent polypeptide compound.

* * * * *